United States Patent [19]

Sibson

[11] Patent Number: 5,728,524
[45] Date of Patent: Mar. 17, 1998

[54] PROCESS FOR CATEGORIZING NUCLEOTIDE SEQUENCE POPULATIONS

[75] Inventor: David Ross Sibson, Amersham, Bucks, United Kingdom

[73] Assignee: Medical Research Counsil, London, United Kingdom

[21] Appl. No.: 367,266

[22] PCT Filed: Feb. 16, 1995

[86] PCT No.: PCT/GB93/01452

§ 371 Date: Jan. 13, 1995

§ 102(e) Date: Jan. 13, 1995

[87] PCT Pub. No.: WO94/01582

PCT Pub. Date: Jan. 20, 1994

[30] Foreign Application Priority Data

Jul. 13, 1992 [GB] United Kingdom ............ 9214873

[51] Int. Cl.6 ............... C12Q 1/68; C12P 19/34
[52] U.S. Cl. ............................ 435/6; 435/91.2
[58] Field of Search ............... 435/5, 6, 91.1, 435/91.2; 935/77, 78

[56] References Cited

U.S. PATENT DOCUMENTS

| | | | |
|---|---|---|---|
| 4,797,355 | 1/1989 | Stabinsky | 435/5 |
| 5,508,169 | 4/1996 | Deugau et al. | 435/6 |

FOREIGN PATENT DOCUMENTS

| | | |
|---|---|---|
| 2 036 946 | 10/1991 | Canada . |
| 0 405 376 | 1/1991 | European Pat. Off. . |

OTHER PUBLICATIONS

Chemical Abstracts, vol. 109, No. 11, Abstract No. 87740j, Sep. 12, 1988.
Chemical Abstracts, vol. 109, No. 20, Abstract No. 184916b, 1988.
Chemical Abstracts, vol. 115, No. 7, Abstract No. 66165h, 1991.
Unrau et al., "Non-cloning amplification of specific DNA fragments . . .", *Gene*, vol. 145, pp. 163–169, 1994.
Biotechniques: 13/74–81 (1992).
Saltman et al, Nucleic Acid Res 20:1401–1404 (1992).
Urdea et al, Nucleic Acid Res 16:4937–4956 (1988).
Haymerle et al, Nucleic Acid Res 14:8615–8624 (1986).

*Primary Examiner*—Eggerton A. Campbell
*Attorney, Agent, or Firm*—Millen, White, Zelano, & Branigan, P.C.

[57] ABSTRACT

A process for the categorization of nucleic acid sequences in which said sequences are linked to a population of adaptor molecules each exhibiting specificity for linking to a sequence including a predetermined nucleotide base, categorization of the resulting linked sequences being based upon selection for the base.

41 Claims, 7 Drawing Sheets

NATURE OF THE CLEAVAGE PRODUCED BY THE
RESTRICTION ENDONUCLEASE FOK 1.

```
  Fok1 site
nnnnggatgnnnnnnnnnnnnnnnnnnnnnnnnnnnnnnn
nnnncctacnnnnnnnnnnnnnnnnnnnnnnnnnnnnnnn
```

→ Restriction endonuclease Fok 1

```
     Fok 1  9 bases
nnnnngatgnnnnnnnnn          nnnnnnnnnnnnnnnnnnnnnnnnn
nnnncctacnnnnnnnnnnnnn      nnnnnnnnnnnnnnnnnnnnnnnnn
              13 bases
``` n — CAN BE ANY BASE BUT IS ALWAYS THE SAME BASE AT ANY POINT IN A GIVEN SEQUENCE OF DNA.

↑↓ SITES OF CLEAVAGE

FIG. 2

EXAMPLES OF ADAPTERS AND PRIMERS USED IN THE SORTING PROCESS.

BIOTINYLATED UNIVERSAL ADAPTOR FOR SPECIFIC ADAPTORS FOLLOWED BY SPECIFIC ADAPTOR OPTIONS

5' Bio GTTCTCGGAGCACTGTCCGAGA 3' or 3' CAAGAGCCTCGTGACAGGCTCT[N]₄[N]₄AA 5'
or 3' CAAGAGCCTCGTGACAGGCTCT[N]₄[N]₄AC 5'
or 3' CAAGAGCCTCGTGACAGGCTCT[N]₄[N]₄AG 5'
or 3' CAAGAGCCTCGTGACAGGCTCT[N]₄[N]₄AT 5'
or 3' CAAGAGCCTCGTGACAGGCTCT[N]₄[N]₄CA 5'
or 3' CAAGAGCCTCGTGACAGGCTCT[N]₄[N]₄CC 5'
or 3' CAAGAGCCTCGTGACAGGCTCT[N]₄[N]₄CG 5'
or 3' CAAGAGCCTCGTGACAGGCTCT[N]₄[N]₄CT 5'
or 3' CAAGAGCCTCGTGACAGGCTCT[N]₄[N]₄GA 5'
or 3' CAAGAGCCTCGTGACAGGCTCT[N]₄[N]₄GC 5'
or 3' CAAGAGCCTCGTGACAGGCTCT[N]₄[N]₄GG 5'
or 3' CAAGAGCCTCGTGACAGGCTCT[N]₄[N]₄GT 5'
or 3' CAAGAGCCTCGTGACAGGCTCT[N]₄[N]₄TA 5'
or 3' CAAGAGCCTCGTGACAGGCTCT[N]₄[N]₄TC 5'
or 3' CAAGAGCCTCGTGACAGGCTCT[N]₄[N]₄TG 5'
or 3' CAAGAGCCTCGTGACAGGCTCT[N]₄[N]₄TT 5'

NON SPECIFIC ADAPTOR COMBINATION

3'[N]₄[N]₄[N]₄AGGAAGAGGACGCTGTCTGT 5'
5' TCCTTCTCCTGGACAGACA 3'

POSSIBLE PRIMERS FOR USE WITH NON SPECIFIC ADAPTOR COMBINATION

3' AAGGAAGAGGACGCTGTCTGT 5'
or 3' CAGGAAGAGGACGCTGTCTGT 5'
or 3' GAGGAAGAGGACGCTGTCTGT 5'
or 3' TAGGAAGAGGACGCTGTCTGT 5'

PRIMER OPTIONS FOR USE WITH SPECIFIC ADAPTORS

5' GTTCTCGGAGCACTGTCCGAGAA 3'
or 5' GTTCTCGGAGCACTGTCCGAGAC 3'
or 5' GTTCTCGGAGCACTGTCCGAGAG 3'
or 5' GTTCTCGGAGCACTGTCCGAGAT 3'

FIG. 4

PROCESS FOR CATEGORIZING NUCLEOTIDE SEQUENCE POPULATIONS

This application is a National Phase filed under 35 USC §371 of PCT GB 93/01452 having priority to United Kingdom Patent No. 9214873.2 filed on Jul. 13, 1992.

This invention relates to a technique designed to facilitate study of the individual members of populations of nucleic acid sequences, particularly where the individual members of such populations may be present in widely varying amounts. This technique permits indexing of sequences.

Situations are increasingly arising in which it is necessary to study complex nucleic acid or polynucleotide populations. For example, it is now widely appreciated that an invaluable resource could be created if the entire sequence of the genomes of organisms such as man were determined and the information available. The magnitude of such a task should not, however, be underestimated. Thus, the human genome may contain as many as 100,000 genes (a very substantial proportion of which may be expressed in the human brain: Sutcliffe, Ann. Rev. Neurosci. 11:157-158 (1988)). Only a very small percentage of the stock of human genes has presently been explored, and this largely in a piecemeal and usually specifically targeted fashion.

There has been much public debate about the best means of approaching human genome sequencing. Brenner has argued (CIBA Foundation Symposium 149:6 (1990)) that efforts should be concentrated on cDNAs produced from reverse transcribed mRNAs rather than on genomic DNA. This is primarily because most useful genetic information resides in the fraction of the genome which corresponds to mRNA, and this fraction is a very small part of the total (5% or less). Moreover, techniques for generating cDNAs are also well known. On the other hand, even supposing near perfect recovery of cDNAs corresponding to all expressed mRNAs, some potentially useful information will be lost by the cDNA approach, including sequences responsible for control and regulation of genes. Nonetheless, the cDNA approach at least substantially reduces the inherent inefficiencies resulting from analysis of repeated sequences and/or non-coding sequences in an approach which depends upon genomic DNA sequencing.

Recently, the results of a rapid method for identifying and characterising new cDNAs has been reported (Adams, M. D. et al., Science 252, 1991, pp 1651-1656). Essentially, a semi-automated sequence reader was used to produce a single read of sequence from one end of each of a number of cDNAs picked at random. It was shown, by comparing the nucleic acid sequences of the cDNAs (or the protein sequences produced by translating the nucleic acid sequence of the cDNAs) to each other and to known sequences in public databases, that each of the cDNAs picked at random, could be unambiguously classified. The cDNAs could be classified as being either entirely new or as corresponding, to a greater or lesser extent, to a previously known sequence. cDNAs identified in this way were further characterised and found to be useful in a variety of standard applications, including physical mapping. Unfortunately, such a process is insufficient. The longer the process is pursued with any given population of cDNAs the less efficient it becomes and the lower the rate of identification of new clones. In essence, as the number of cDNAs which have already been picked rises, the probability of picking a particular cDNA more than once increases because of the wide range of abundancies at which different cDNAs are found, which abundancies can vary by several orders of magnitude. Thus, whereas some sequences are exceedingly rare, a single cDNA type may comprise as such as 10% of the population of cDNAs produced from a particular tissue (Lewin, B. Gene Expression, Vol. 2: Eucaryotic Chromosomes, 2nd ed., pp. 708-719. New York: Wiley, 1980). The need to avoid missing rarer species in any given population presents a considerable problem.

Various approaches have been tried in addressing the problem of increasing the efficiency of examination of a mixed nucleotide population, for example, such a population as is to be examined in human genome sequencing.

Thus, a standard PCR protocol can be used to amplify selectively cDNAs which are present at extremely low levels, if there is information about the sequence of those cDNAs. If not, a primer specific to the desired cDNA cannot be constructed and the desired cDNA cannot be selectively amplified. The standard PCR method is therefore inadequate if it is desired to characterise a number of unknown genes.

Other approaches attempt to produce a more uniform abundance of the members of a population of cDNAs, so-called "normalization methods". A first approach involves hybridization of cDNA to genomic DNA. At saturation, the cDNAs recovered from genomic/cDNA hybrids will be present in the same abundance as the genes encoding them. This will provide a much more homogenous population than the original cDNA library, but does not entirely solve the problem. In order to reach saturation in respect of the very rare sequences, it will be necessary to use huge quantities of cDNA, which need to be allowed to anneal to large amounts of genomic DNA over a considerable period of time. Furthermore, cDNAs which have homology to parts of the genome which are present in multiple copies will be over-represented.

A second approach exploits the second order reassociation kinetics of cDNA annealing to itself. After a long period of annealing, the cDNAs which remain single stranded will have nearly the same abundance, and can be recovered by standard PCR (see Patanjali, S. R. et al., PNAS U.S.A. 88, 1991, pp. 1943-1947; Ko, M. S. H., NAR 19, no. 18, 1991, pp 5705-5711). The methods disclosed in these two publications, however, suffer from notable disadvantages. They are entirely dependent on the stringent physical separation of single stranded and double stranded DNA, require an elevated number of manual manipulations in each reaction, and necessitate protracted hybridisation times (up to 288 hours in the method of Patanjali et al.)

Yet a further approach in "normalizing" a nucleotide population is described in copending British Patent Application No 91 15407.0, filed 17th Jul. 1991 by MRC, and involves a PCR process in which a mixture comprising a heterogenous DNA population and appropriate oligonucleotide primers is first formed and the DNA denatured, but before effecting a conventional PCR protocol the conditions are altered to allow the denatured strands of the more common DNA species to reanneal together, whilst avoiding annealing of primers to the DNA strands. By this means, rarer species can subsequently be amplified in preference to the more common species.

This PCR normalization method in general comprises the steps of:

(a) preparing a mixture comprising a heterogenous DNA population and oligonucleotide primers suitable for use in a PCR process, in which the DNA is denatured;

(b) altering the conditions to allow the denatured strands of the more common DNA species to reanneal, while preventing the annealing of the primers to the DNA strands;

(c) further altering the conditions of the mixture in order to allow the primers to anneal to the remaining single-stranded DNA comprising the rarer DNA species; and (d) carrying out an extension synthesis in the mixture produced in step (c).

Advantageously, the method consists of a cyclic application of the above four steps.

It will be appreciated that the conditions may be altered by the alteration of the temperature of the reaction mixture. However, any conditions which affect the hybridization of complementary DNA strands to one another may be varied to achieve the required result.

Because the reannealing efficiency of any given DNA species will depend on the product of its concentration and time, the more abundant the sequence the greater the extent to which it will reanneal in any given time period. Once a DNA species has reached a certain threshold concentration it will no longer be amplified exponentially, as a significant amount will have annealed to the double stranded form before the priming step. Thus, as each individual DNA species is amplified by the process to its threshold concentration, the rate of amplification of that species will start to tail off. Eventually, therefore, all DNA species will be present at the same concentration.

The length of the reannealing step will determine how much DNA is present at the threshold concentration. Preferably, therefore, the duration of the reannealing step will be determined empirically for each DNA population.

In the PCR normalization process in general, the DNA primers may be adapted to prime selectively a sample of the total DNA population. By using primers which will only prime a sample of the population, only that sample will be amplified and normalised. The total quantity of DNA generated will thereby be reduced, which means that the cycling times can be kept low. This ensures that the method is applicable to complex DNA populations such as cDNA populations. In addition, a first primer can be used which is adapted selectively to prime a sample of the total cDNA population, and a second primer which is a general primer. Advantageously, the general primer is oligo dT (each primed cDNA will then be replicated in its entirety, as the oligo dT primer will anneal to the poly-A tail at the end of the cDNA).

The present invention now provides a new process which allows the study and identification of the individual members of a mixed or heterogenous population of nucleic acid sequences perhaps of varying abundance, for example, the efficient identification of most cDNAs from a given source tissue of a complex organism such as a human being. The process of the invention is particularly adapted to facilitate sorting (and investigation) of rarer sequences in a population. Furthermore, nucleic acid sequences, for example cDNAs as mentioned above, are produced in the process in a way which makes them useful for new, convenient and powerful approaches to a wide variety of other applications.

Accordingly, the present invention provides a process for categorizing uncharacterised nucleic acid by sorting said nucleic acid into sequence-specific subsets, which process comprises:

(a) optionally, initially subjecting said uncharacterized nucleic acid to the action of a reagent, preferably an endonuclease, which reagent cleaves said nucleic acid so as to produce smaller size cleavage products;

(b) reacting either the uncharacterized nucleic acid or, as the case may be, cleavage products from (a) with a population of adaptor molecules so as to generate adaptored products, each of which adaptor molecules carries nucleic acid sequence end recognition means, and said population of adaptor molecules encompassing a range of such molecules having sequence end recognition means capable of linking to a predetermined subset of nucleic acid sequences; and (c) selecting and separating only those adaptored products resulting from (b) which include an adaptor of chosen nucleic acid sequence end recognition means.

In the above process, the adaptor molecules preferably comprise oligonucleotides in which single stranded ends of known nucleotide composition are present (the "nucleic acid sequence end recognition means" of the above process definition), said single stranded ends each exhibiting complementarity to a predetermined nucleic acid end sequence or end nucleotide so as to permit linkage therewith.

Of course, other forms of adaptor molecule can be envisaged. For example, adaptors can be chosen which are capable of specific reaction, preferably by covalent means, to any particular nucleotide or nucleic acid base or bases. Thus, advantage can, if desired, be taken of the existence of unusual bases in certain nucleic acids, for instance, 5-hydroxymethylcytosine or thionucleotides. The nature of the linkage between adaptor and nucleic acid resulting from step (b) of the present process is irrelevant to success in the present invention, provided that such linkage is sufficiently strong to permit step (c) to be carried out, and further provided that the linkage is specific in a known way to only a known category of nucleic acid sequence ends or end nucleotides.

The process of the present invention can be applied to double stranded or single stranded nucleic acid materials, and there is no other particular limitation on the nature of the starting "uncharacterized" material which can be treated in the present process.

Preferably, step (b) of the present process is carried out with a population of adaptor molecules such that both ends of uncharacterized nucleic acid sequences or of the cleavage products from (a) can be adaptored in a known way.

At least some of the adaptor molecules of the present invention can be structured so as to permit physical separation in step (c) of the present process by immobilizing adaptored products on a solid phase. As an alternative, adaptor molecules can be used which comprise (in addition to their sequence end recognition means) a known sequence permitting hybridization with a PCR primer. In such embodiments, the application of PCR techniques to a mixture of adaptored products, using primers of preselected sequence, effectively enables one or more predetermined subset(s) of sequences to be selected.

It will be appreciated that the starting nucleic acid material in the process of the present invention may already be in the form of a population of separate nucleic acid sequences. Alternatively, even a lengthy continuous molecule, such as a complete chromosome, can be employed and, in order to produce a population of sequences for sorting and categorization, the optional cleavage step of the present process, step (a), can be carried out.

If optional step (a) is effected, and if the reagent used for cleavage purposes is an endonuclease, this may be an enzyme specific to double stranded materials or it may be an enzyme which has the capability of cutting at a recognized sequence on a single stranded product, depending upon the substrate uncharacterized nucleic acid.

Examples of suitable restriction endonucleases which recognize single stranded DNA and which also leave a cleaved sequence overhang when cutting double stranded sequences (see later), which overhang is at least partly degenerate, include, BstNI, DdeI, HgaI, HinfI and MnlI.

Thus, for example, HgaI leaves a 5 base overhang starting 5 bases from the cut site, and MnlI cuts 7 bases away, but only leaving a 1 base overhang. Single stranded cleavage can also be achieved for enzymes which do not naturally cut single stranded DNA by annealing to the single strands an oligonucleotide containing a sequence for the recognition site for the enzyme, and which thus provides a partial double strand of sufficient length and nature for the enzyme to cut both strands.

One aspect of the power of the present pioneering process is the very generality of the materials which can be examined in applying, for the first time, an efficient technique for categorising and sorting nucleic acid sequences. Indeed, depending upon the number of stages in any sorting/selection process carried out (and the following description gives guidance as to various means whereby additional and further degrees of selection may be achieved), it is perfectly within the scope of preferred embodiments of the present invention to envisage adaptor molecules wherein the specificity is determined only by one nucleotide base available for linkage to an uncharacterised nucleic acid sequence end (eg specific to the final nucleotide).

As will be described hereinafter, the ability to sort/select to a high degree by sorting/selecting in various stages is another great benefit of this invention. There is an exponential relationship between the number of such stages and the degree of sorting/selection.

One preferred aspect of the present invention is a process of categorising uncharacterized nucleic acid, which process comprises:

(a) subjecting said uncharacterized nucleic acid to the action of a reagent, preferably an endonuclease which has cleavage and recognition site separated, which reagent cleaves said nucleic acid so as to produce double stranded cleavage products the individual strands of which overlap at cleaved ends to leave a single strand extending to a known extent;

(b) ligating the cleavage products from (a) with adaptor molecules to generate adaptored cleavage products, each of which adaptor molecules has a cleavage product end recognition sequence and the thus-used adaptor molecules encompassing a range of adaptor molecules having recognition sequences complementary to a predetermined subset of the sequences of the cleavage-generated extending single strands; and (c) selecting and separating only those adaptored cleavage products resulting from (b) which carry an adaptor of known recognition sequence.

The above preferred process of the present invention, aside from the general advantages of selection and sorting, additionally provides the extremely important advantage of being a means of indexing sequences because it enables a "marker" (in the form of a specific adaptor—see later) to be positioned at a predetermined site in any sequence. Furthermore, for the first time, sequence subsets can be produced in which not merely is something known about the individual sequence "ends", but also directionality in the sequences is established.

Generally, in the present invention it is convenient to use a population of adaptors simultaneously in step (b). Of course, if circumstances dictate, or if it is preferred for any reason, separate reactions may be performed with subsets of the total possible adaptor molecules required for "adaptoring" all possible sequence types.

In the present invention, "uncharacterized nucleic acid" is simply intended to mean any nucleic acid or population of nucleic acid sequences which is/are of partially or wholly unknown sequence.

As mentioned above, it is not significant to the generality of the present invention whether the uncharacterized nucleic acid is double stranded or single stranded. However, in what follows a category of preferred embodiments of the invention is described in which Fok 1 is used as an endonuclease to generate nucleic acid fragments in accordance with step (a). If it is desired to use such an enzyme, or a similar enzyme, and the uncharacterized nucleic acid which it is desired to categorise consists of single stranded sequence material, such single stranded material can first be converted to double stranded sequences by methods known in the art (see, for example, Sanger, F. et al., Proc. Natl. Acad. Sci. 74, 1977, p5463–5467, Zoller, M. J. and Smith, M. Methods Enzymol. 100, 1983, p468–500, Gubler, U. and Hoffman, B. J. Gene 25, 1983 p263–269). The extent of strand overlap at the end of cleavage products resulting from step (a), in preferred embodiments, if carried out on double stranded material, may be as little as a single base, but is preferably two to ten bases, more preferably four to six bases. Preferably, as many as possible (at least 50%, and ideally 95% or more) of the cleavage products from (a) have each end overlapping in this way, and hence are capable of being "adaptored" by the preferred types of adaptor.

Preferred reagents which can be employed in step (a) are endonucleases, preferably Class II restriction endonucleases with cleavage sites with which are asymmetrically spaced across the two strands of a double stranded substrate, and the specificity of which is not affected by the nature of the bases adjacent to a cleavage site.

When using the preferred oligonucleotide adaptator molecules of the invention, although any means of sequence-specific cleavage can preferably be used, most preferably the site of cleavage is not determined by sequence entirely at the ends of the fragments on the ends of different cleavage products. Sequence specific chemical cleavage has been reported (Chu, B. C. F. and Orgel, L. E. Proc. Natl. Acad. Sci. p963–967 (1985)), but the preferred reagents are, as indicated above, a subset of Type II restriction endonucleases. This subset includes enzymes that have multiple recognition sequences, enzymes that recognise interrupted palindromes and enzymes that recognise non-palindromic sequences. Type II restriction endonucleases of these types together cover a wide range of specificities, are readily available, and are highly specific and efficient in their action (Review: Roberts, R. J. Nucl. Acids res. 18, 1990, p2331–2365). Some enzymes of the required type are listed in Table 1 below.

TABLE 1

| Enzymes with Multiple Recognition Sequences | Enzymes that Recognise Interrupted Palindromes | Enzymes that Recognize Nonpalindromic Sequences | |
|---|---|---|---|
| Acc I | AlwN I | Alw I | GGATC(4/5) |
| All III | Bgl I | Bbs I | GAAGAC(2/6) |
| Aja II | BsaB I | Bbv I | GCAGC(8/12) |
| Ava I | BsaJ I | Bsa I | GGTCTC(1/5) |
| Ban I | BstE II | Bsm I | GAATGC(1/−1) |
| Ban II | BstX I | BsmA I | GTCTC(1/5) |
| BsaA I | Bsu36 I | BspM I | ACCTGC(4/8) |
| Bsp1286 I | Dra III | Bsr I | ACTGG(1/−1) |
| BstY I | Drd I | Ear I | CTCTTC(1/4) |
| Clr10 I | EcoN I | Eco57 I | CTGAAG(16/14) |
| Dsa I | EcoO109 I | Fok I | GGATG(9/13) |
| Eae I | Esp I | Gsu I | CTGGAG(16/14) |
| Gdl II | Nla IV | Nga I | GACGC(5/10) |
| Hae II | PflM I | Hph I | GGTGA(8/7) |
| HglA I | PpuM I | Mbo II | GAAGA(8/7) |
| Hinc II | Sfi I | Mme I | TCCRAC(20/18) |
| NspB II | Tth111 I | Mnl I | CCTC(7/6) |
| NspH I | Xcm I | Ple I | GAGTC(4/5) |
| Sty I | Xmn I | Sap I | GCTCTTC(1/4) |

TABLE 1-continued

| Enzymes with Multiple Recognition Sequences | Enzymes that Recognise Interrupted Palindromes | Enzymes that Recognize Nonpalindromic Sequences | |
|---|---|---|---|
| Rsr II | Sfi I | SfaN I | GCATC(5/9) |
| | | Taq II | GACCGA(11/9) |
| | | Tth111 | ICAARCA(11/9) |

Cleavage sites for enzymes which cleave outside of their recognition sequence are indicated in parentheses. For example, GGTCTC(1/5) indicates cleavage at:
5' ...GGTCTCN▼...3'
3' ...CCAGAGNNNNN▼...5'

Cleavages produced by some enzymes are blunt, while others produce a terminus with a single-stranded extension. Preferred enzymes fall into the latter category because these allow base specific ligation to be used for sorting into subsets without having to produce single-stranded extensions from blunt ended termini.

As indicated earlier, a preferred endonuclease for use in the present invention is Fok 1.

An important feature of the present process is the use of adaptor molecules. The preferred adaptors generally have "overhanging" fragment recognition sequences which reflect or are complementary to the extending cleavage-derived sequences which the adaptors are designed to react with. It is also preferred that such adaptors should end with a 5' hydroxyl group. The avoidance of a 5' phosphate group removes the risk of inappropriate ligation involving the adaptors. Alternatively, fragments to be adaptored should have their 5' phosphates removed and adaptors which have the potential to ligate to each other should be chosen so as to be separable by a means known in the art.

Adaptor molecules may also contain a portion permitting specific sequence selection and separation (as in step (c) of the present process) when a sequence is attached to the adaptor. For example, an adaptor can carry biotin, thereby permitting advantage to be taken of the biotin/avidin reaction in selecting and separating desired adaptored molecules. Additionally, adaptors preferably comprise a known and selected sequence such that specifically adaptored molecules can be amplified by known techniques (such as PCR) using a primer complementary to the core sequence.

Preferably adaptors in the invention are short double-stranded oligonucleotides which can be joined to the ends of cleavage products. They will have been chemically synthesised so that their sequence can be predetermined and so that large concentrations can be easily produced. They may also be chemically modified in a way which allows them to be easily purified during the process. As mentioned above, ideally their 5' ends will be unphosphorylated so that once joined to fragments the adaptored end of the latter will no longer be able to participate in further ligation reactions.

[Preferably, all ligation reactions used in the invention will be catalysed by DNA ligase, since this enzyme is readily available and easy to use.]

It is preferred that the adaptor cleavage product end recognition sequences are on the 5' end of the longest oligonucleotide strand making up the preferred adaptor molecules, are at least 3 nucleotides in length and with totally random bases at the single stranded position(s) two nucleotides in from the 5' end. This then allows selection to be performed both during the joining reaction and during subsequent priming reactions. Then, because the final degree of selection is a result of the product of the degrees of selection achieved at these two stages, maximum selection can be achieved per adaptor/primer available (see later for further discussion).

Adaptor strand extensions on the 5' end of the longest oligonucleotide also facilitate the use of modified oligonucleotides for separation purposes. Preferably, the short oligonucleotide will be modified at its 5' end. This has the double benefit of requiring just one modified oligonucleotide for all possible single-stranded extensions that are used, and also placing the modification at a position where it cannot interfere with ligation or subsequent priming reactions.

Although only one type of adaptor is required per ligation reaction, it is preferred that adaptors covering all possible reactions in a chosen subset of sequences be present, because then the opportunity for fragments in the chosen subset to ligate to each other is minimised. It is also preferred that the chosen specific adaptor, carrying a predetermined recognition sequence, should not only be different from the other adaptors in its single-stranded extension, but also different in the rest of its sequence since this allows orientation to be introduced which is useful in subsequent steps. It is therefore also preferred that this adaptor has a modified oligonucleotide to facilitate its separation with the cleavage products to which it joins.

The process of the invention can be used to generate categories or subsets of sequences by making some of the adaptors specific in some way, and selecting and separating as in step (c). In this way subsets of sequences can be provided depending upon the specific adaptor chosen, e.g. for use in subsequent nucleotide sequencing. This facilitates, for example, the identification of a large population of sequences by permitting a rational approach to splitting such populations into subsets, each of which subsets can be examined in turn.

It will, of course, be appreciated that a subset generated in the present process can be regarded as a known fraction or specific proportion of all sequences in the original uncharacterized nucleic acid. A number of considerations can be used in determining the size and nature of any particular subset. For example, subsets should not be too small because if the original nucleic acid provides a considerable number of different sequences, increasing the number of subsets also increases the number of adaptors and primers necessary and the number of experiments needed in order to categorize the nucleic acid. On the other hand, the person of skill in the art will need to tailor the subset size to give the required degree of resolution for any intended application. This is a matter of choice by the person of skill in the art, rather than general guidance.

Preferably there are only on average as many members of a subset as it would be convenient to identify in a later application of the present process, for example random picking for identification by sequencing. In this context, it is preferred that there be no more than a thousand members, preferably no more than five hundred members in a subset. A further point in relation to subset size is that it may be required to label simultaneously the subset for use as a probe. Preferably, in such a case, the total subset size should not exceed 500 kilobases, although this may be provided in a number of ways, e.g. 500 different 1 kilobase sized sequences or, for example, 1000 different 500 base sized sequences. Again, the matter is one of choice to the skilled operator.

It should also be remembered that adaptors are designed and required in the present process to ligate the fragments. In some circumstances, this can be driven kinetically e.g. by the presence of large concentrations of adaptor. When this happens, subsets must be chosen so that the concentrations or diversity of fragments is such that the range of fragment ends available permits the desired adaptor concentrations to be attained.

This invention includes both the new adaptor molecules described herein, and also kits for performing a process of the invention which comprise a group of such adaptors designed to adaptor a predetermined group of nucleic acid sequences. In some embodiments, the present kits include a plurality of groups of different adaptors. The kits of the invention may also include, inter alia, a nucleic acid cleavage reagent, eg Fok 1 or other endonuclease as above, and/or PCR primers.

The new categorization process of the invention will now be described further in relation to the accompanying drawings.

As will be appreciated, in the description that follows, including the specific Example, many individual features are referred to which are of broader applicability in carrying out embodiments of this invention than merely in performing any particularly described work.

In the drawings:

FIG. 2 shows the cleavage behaviour of a preferred endonuclease for the invention, Fok 1;

Figure 5A:
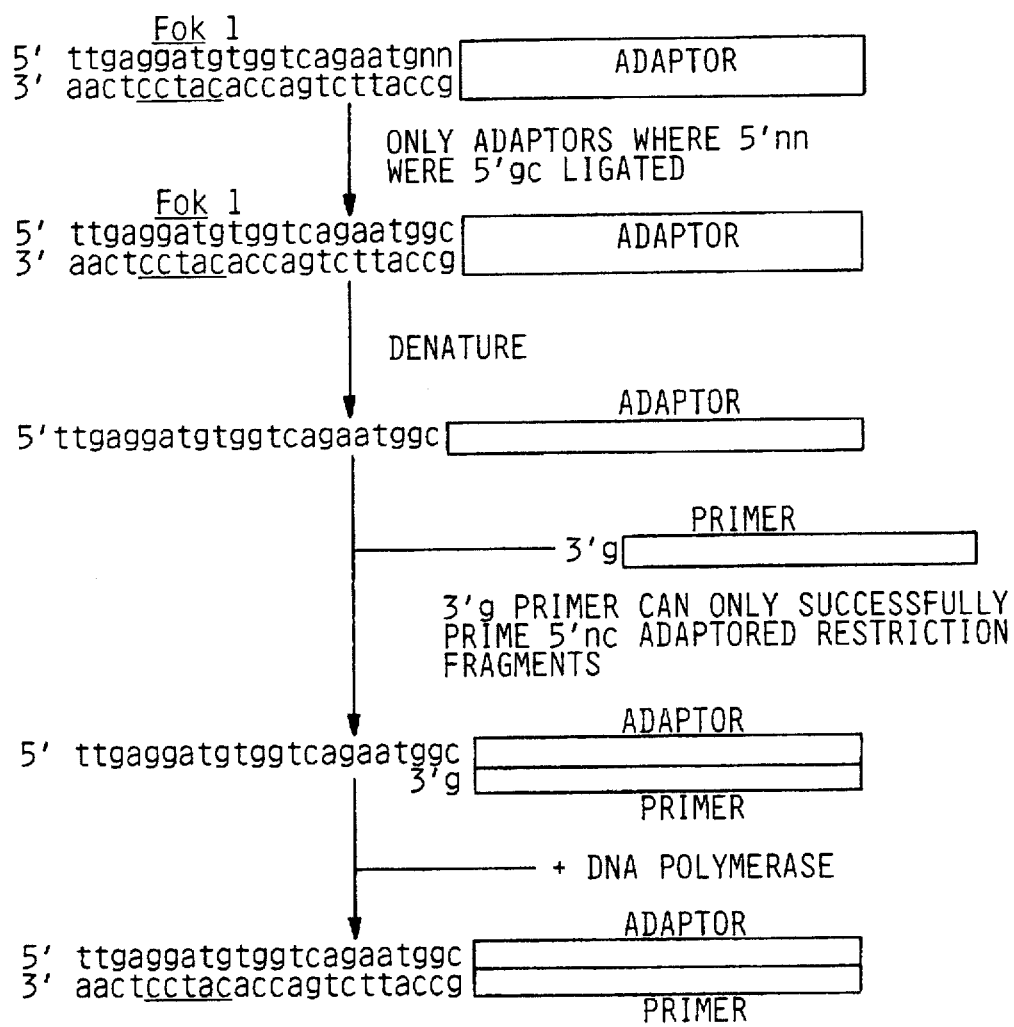
Figure 5B:
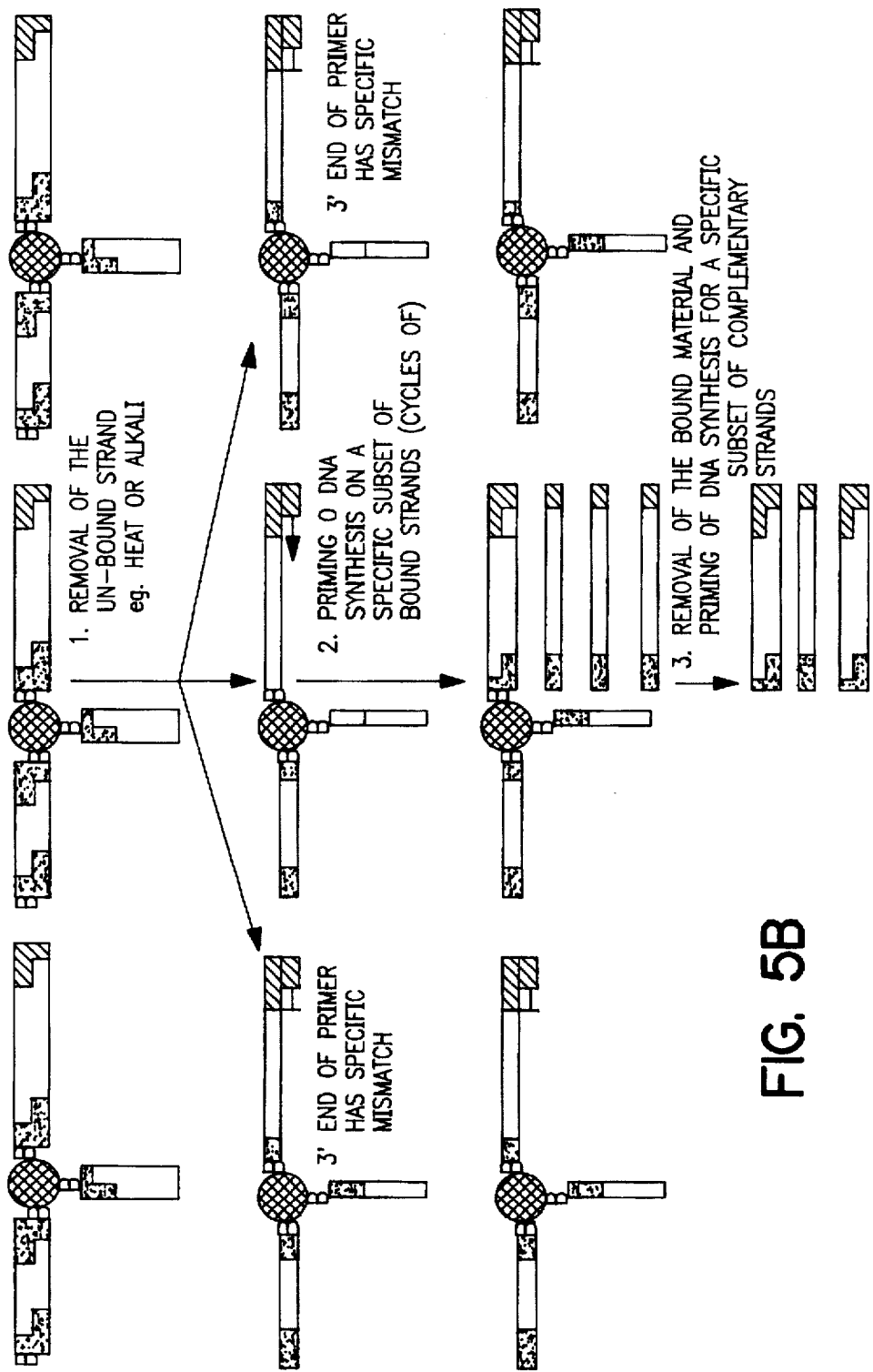

FIG. 4 lists a range of adaptors and primers which can be used in the present invention; and FIGS. 5a and 5b show specific predetermined priming (for amplification purposes) of specifically adaptored molecules.

Figure 1:
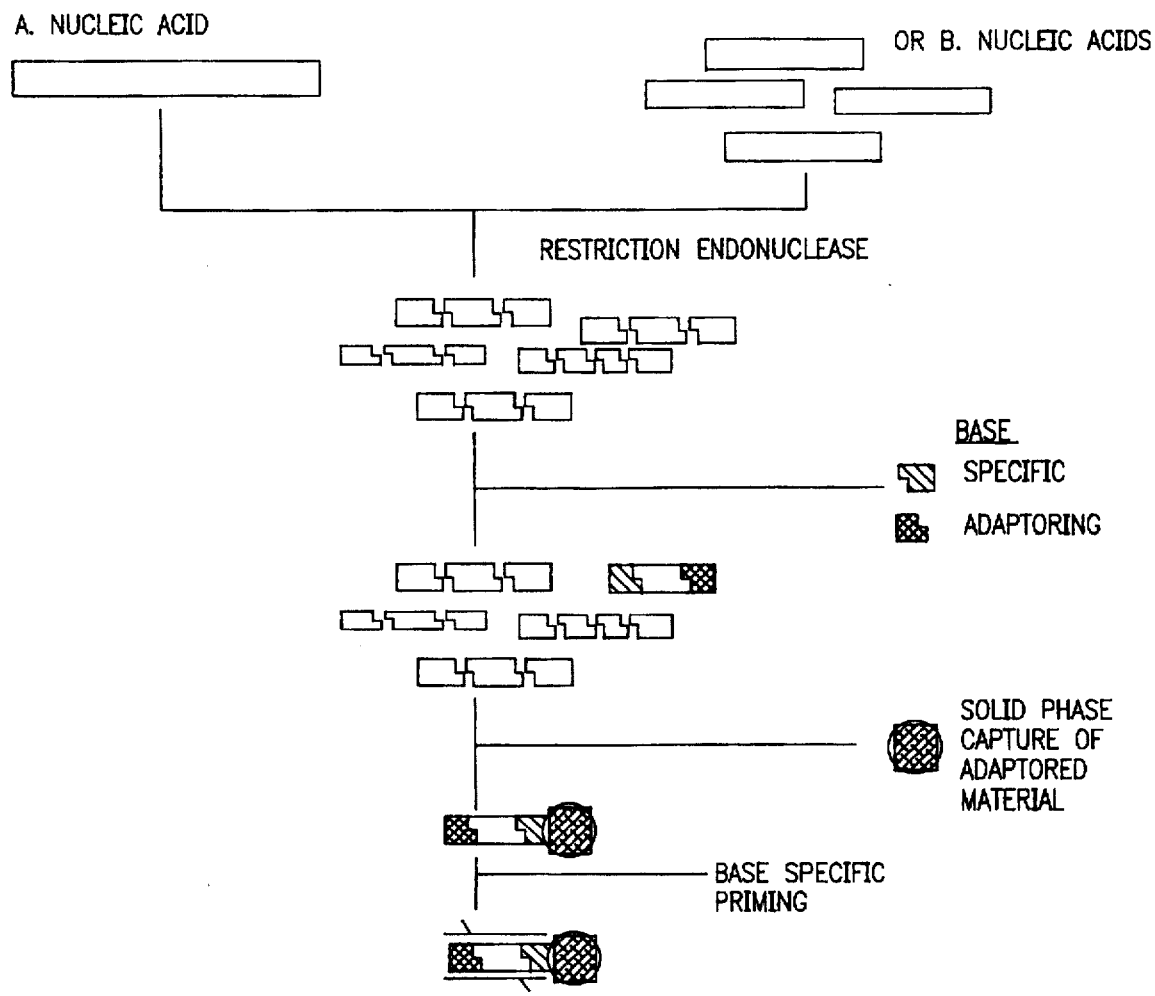
FIG. 1 is a schematic representation of a basic procedure behind the process of the invention for selection specific fragments—for simplicity it does not show all the adaptors which would be used in practice.

The process of the present invention is shown in outline in FIG. 1. A nucleic acid or population of nucleic acids is cleaved with a selected restriction endonuclease of known specificity and cleavage characteristics. The preferred example is Fok 1. The cleavage behaviour of Fok 1 is illustrated in FIG. 2, and it will be seen that the single-stranded overhang or extension produced at the cleaved ends as a result of the action of Fok 1 can be any one of 256 possible four base sequences. However, at a given cleavage site the sequence will always be the same. Fok 1 is useful in this respect, both because it generates an overhang as illustrated in FIG. 2 and also because its cleavage and recognition sites are separate.

The next stage in the process is the reaction of the population of nucleic acid sequence fragments resulting from endonuclease action with a population of adaptors. For the sake of simplicity, FIG. 1 shows only the use of two specific adaptors, but it will be appreciated that for the purpose of categorizing sequences in a mixed population or normalising such sequence populations, all possible adaptors specific for a predetermined subset of sequences must be used. This aspect will be referred to again hereinafter.

In FIG. 1 one of the base specific adaptors is shown as being able to attach to a solid phase, and this attachment permits capture of fragments which have been adaptored by the specific adaptor in question. Thereafter, amplification techniques, e.g. PCR, may be used for base specific priming and amplification of the thus-isolated fragments.

When adaptoring is performed, it is important that all permutations of adaptor overhang be present or there will be the potential for hybrid molecules to form which are not representative of the original nucleic acid or nucleic acid population. Such hybrid molecules can form when fragments which have not been specifically adaptored ligate to each other or to the free ends of fragments which have been adaptored in a specific way.

Figure 3A:
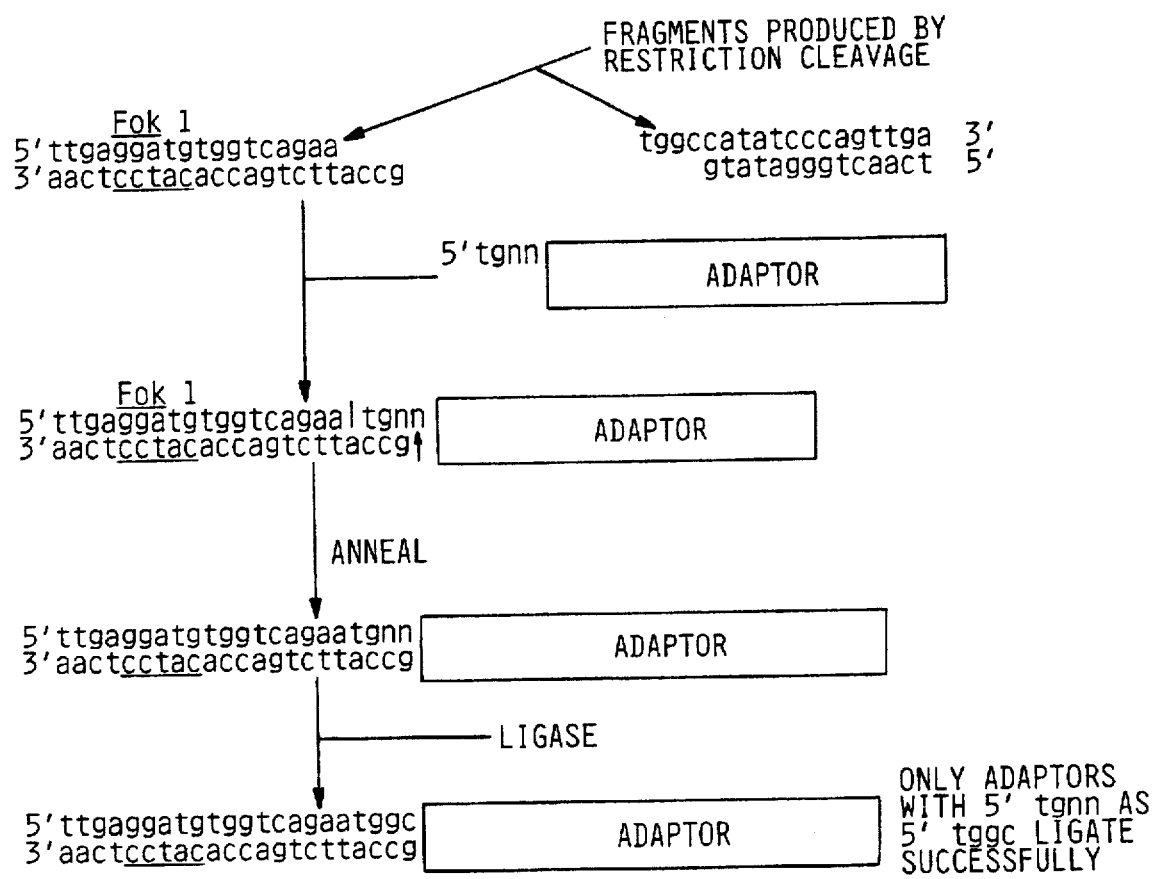
FIG. 3a illustrates the use of specific adaptors in accordance with the present process.
Figure 3B:
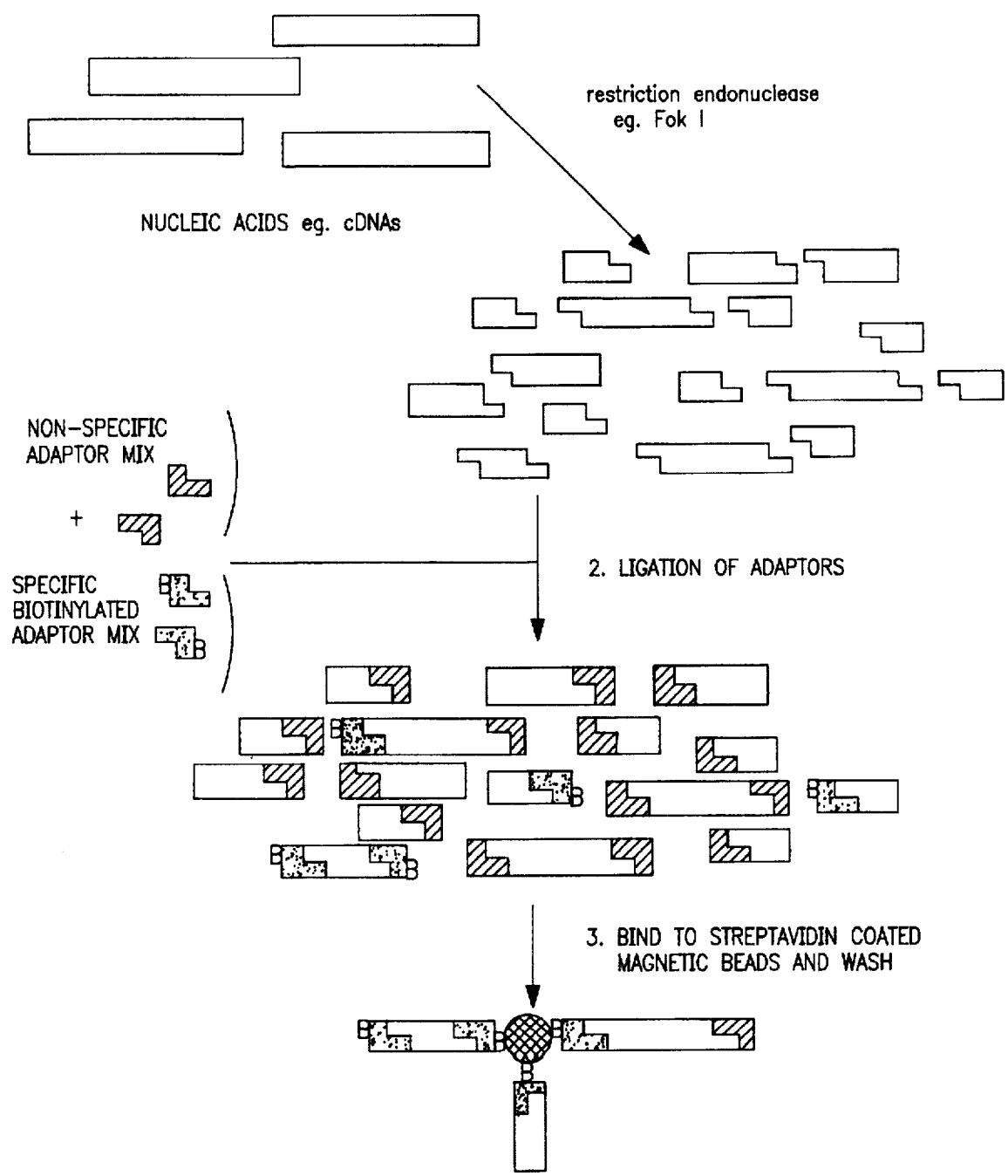
FIG. 3b illustrates the selection of specifically adaptored sequences after endonuclease digestion.

As can be seen most clearly in FIGS. 3a and 3b, it is at the stage of adaptoring that the process of the invention introduces sorting or categorizing of the fragments derived from endonuclease action. Obviously, any given adaptor will only react with a cleaved sequence where the overhang is complementary to the recognition sequence of the adaptor. A degree of selection can thus be introduced at this point by preselecting one or more of the bases of the adaptor cleavage product end recognition sequence. Clearly, such specific adaptors are only capable of ligating with cleavage products or fragments in which the overhang or extending sequence has a complementary base at the appropriate position or positions. This limits the proportion of the fragments resulting from endonuclease activity which can be adaptored by the specific adaptors.

A successful adaptoring stage in the present process depends upon the use of a restriction endonuclease which can produce any combination of bases in cleavage product ends. Clearly, if the overhanging bases were the same on all products or fragments resulting from cleavage, no selection would be possible.

As can be seen most clearly from FIG. 3b, if a mixture of non-specific adaptors and specific adaptors is employed, and the specific adaptors are labelled or otherwise enabled in some way to be separated from the resulting mix, a subpopulation of fragments is thereby automatically selected which has one or more predetermined bases in the overhang or single stranded extension at each cleavage site, which base or bases are predetermined by the choice of complementary base or bases in the recognition sequences of the adaptors.

As can be seen in FIG. 3b, if specific adaptors are biotinylated, the adaptored molecules which carry biotin residues can be bound to streptavidin-coated magnetic beads, washed and separated. Of course, other separation systems and labelling systems known in the art can be employed, and this is a matter of choice for the skilled reader (Uhlen, M., Nature 340, 1989, pp 733–744).

It will also be appreciated that although the technique illustrated in FIG. 3b shows only one category of specific adaptor, which specific adaptor employs biotin/streptavidin in an art-understood way to isolate only those fragments to which the adaptor will bind, a number of specific adaptors can be employed simultaneously, provided such specific adaptors (and molecules to which they are attached when adaptoring has occurred) can be separated from each other.

In a subsequent stage of preferred process of the invention, if desired after the specifically adaptored fragments have been separated, a further degree of selection can be achieved by copying or amplifying only selected subsets of the subset of specifically adaptored nucleic acid fragments. Initial physical separation is, of course, not strictly necessary if a PCR-type process using only selected primers is employed. In any event, this further selection depends upon predetermined sequences in the core portion of the specific adaptors. Thus, once a particular set of specific adaptored molecules has been isolated, for example by being bound to a solid phase using the biotin/streptavidin system, the nucleic acid fragments thus immobilised can be copied/amplified using a primer complementary to and specific for the core sequence of adaptors attached to immobilized nucleic acid fragments at their ends remote from the sites of immobilisation. Such primers preferably extend by one or more specific extra bases into the adaptored fragment.

As a result of this technique for further selection, only those adaptored fragments can be copied which carry at their unbound ends the appropriate adaptor, preferably only those fragments having a sequence complementary to the chosen extra base or bases on the primer.

In this further selection technique it is highly preferred to use a polymerase which cannot significantly synthesize new strands from incorrectly annealed primers nor remove incorrectly annealed bases. Suitable enzymes include AMV reverse transcriptase (Kacian, D. L., Methods Virol. 6, 1977, p143), M-MLV reverse transcriptse (Roth, M. J. et al., J. Biol. Chem. 250, 1985, p9326–9335), DNA polymerase 1 Klenow (Exonuclease-Free) (Derbyshire, V., et al., Proc. Natl. Acad. Sci. U.S.A. 74, 1988, p5463–5467), genetically engineered T7 DNA polymerase ((Sequenase™) Tabor, S. and Richardson, C. C. J. Biol. Chem. 264, 1989, p6447–6458, U.S. Pat. No. 4,795,699), and Taq DNA polymerase (Lawyer, F. et al., J. Biol. Chem. 264, 1989, p6427–6437).

Preferably, yet further selection can be achieved by selecting subsets of the resulting newly synthesized molecules. To do this, base specific priming can be carried out as described above, except that the template for the primer in question is not the adaptor remote from immobilisation of the fragment, but rather the core portion sequence of the adaptor originally bound to the solid support. It will be appreciated that molecules obtained by copying at the first stage of selection subsequent to step (c) of the basic process of the invention are single stranded. A yet further stage of selection renders selected fragments double-stranded, and such fragments can be cloned by standard techniques see, for example, "Molecular Cloning", 2nd Edition Sambrook J., Fritsch, E. F., and Maniatis, T. CSH Press (1989).

The process of the invention can thus be used not merely to categorise molecules but also to select in a series of stages, hence "enriching" the amount available of any particular fragment. The final degree of enrichment depends upon the number of bases specifically predetermined at the adaptoring and priming stages. By way of example, if two rounds of priming are employed, and if a specific adaptor is used which is specific for a single base and the first primer is specific for one base and the second primer is specific for two bases, the level of enrichment resulting from selection is 128 fold. This is because although each of the pre-determined or pre-selected bases which gives a single point of selection is one of four possibilities (giving a total number of permutations of 256), account must be taken of the fact that each fragment has two ends which are capable of being adaptored, thus dividing the degree of enrichment in half. It will be appreciated by those of skill that the same degree of enrichment can be achieved by using different combinations. For example, again assuming two rounds of priming, an adaptor which is specific for two bases only requires primers each specific for a single base in order to achieve 128 fold enrichment.

Not only is it important that the pre-determined bases should not be the same when determining or planning a particular degree of enrichment, it is also advantageous that the base permutations used for selection be distributed or "spread" in as many ways as possible since this minimises the number of primers and adaptors required. For example, a panel of 256 sequence subsets achieving 128 fold enrichment of a desired sequence each could employ a total of 256 base specific adaptors each of which is specific for one of the possible four bases in its "overhang". It is preferable, however, to use, for example, 16 adaptors which are specific for 2 bases each, together with 4 primers each specific for a single base at the 3' end of one of the adaptors and 4 more primers each specific for a single base at the 3' end of the other adaptor. This requires a total of only 24 adaptors and primers, corresponding to more than a ten fold reduction in the amount of these reagents required.

It will be appreciated that the shorter the individual members of any population of nucleic acid sequences of interest, the greater the percentage of nucleic acids which will only be cleaved once by the action of any chosen endonuclease. If most individual nucleic acid sequences in a population are not cleaved twice (or more) they will not be amenable to a full range of selection/enrichment choices in accordance with the principles set out above. Schematically, the presence in the cleavage population of some fragments which do not lend themselves to adaptoring at both ends (as a result of a single cleavage only) is shown in FIG. 3b. This problem can be addressed, if desired, by using two or more different restriction endonucleases, separately or together. Moreover, the present process is "adjustable" by the choice of an enzyme or enzymes where the spacing between recognition site and cleavage site is a favourable distance having regard to the size of the nucleic acid sequences in the chosen population (if known).

Once subsets of nucleic acid sequences have been produced using the present process, they can be employed in a variety of ways. Labelled sequence subsets can be employed as probes, and libraries of subsets can be produced by cloning techniques. In addition, the subsets of sequences can themselves be probed after immobilization using standard techniques (see, for example, "Molecular Cloning" Maniatis et al, supra.)

The present process can be applied to a suitable source material to produce subsets of restriction fragments, clones being picked at random for sequencing from the subsets, examining the subsets one by one. Once any particular subset becomes "exhausted" as an apparent source of new clones (or, more accurately, the rate of recovery of new sequences drops) fresh subsets can be examined. A Poisson distribution can be used to describe the frequencies with which clones are picked at random from a subset in which members are present in equivalent proportions. Such a distribution is, of course, skewed when members are not present in equivalent amounts, the skew being dependent upon the actual differences in the amounts. The observed distribution can be used to calculate the probability of picking at random new members of the subset, and this information can be used to decide whether to persevere with a set for the purpose of picking new members. If the intention is to identify yet more members of a given subset, this may be more efficiently achieved by using a probe prepared using a pool of the already picked clones to identify clones which have not already been picked and contain new sequences. The small sizes of the subset libraries which have to be probed in this way make this technique particularly convenient compared to having to probe a library fully representative of the original starting nucleic acid.

It will be appreciated that the PCR normalization technique described above can be applied to subsets produced by the process of the invention, rather than to the starting nucleic acid population or library, thus shifting the balance of nucleic acid sequences in individual subsets in favour of rarer sequences.

In investigating cDNAs from a tissue source, it is also useful to be able sequence such cDNAs from points other than their ends. In this way, a bias can be introduced in favour of potentially more interesting coding regions. The process of the present invention has the advantage of introducing such bias.

Fundamentally, however, the advantages of the process of the present invention include indexing sequences with consequent great advantages for understanding the structure of new sequences and mapping, and allowing cDNAs to be systematically picked from mRNAs prepared from an entire tissue or even an entire organism whilst increasing the "yield" of different sequences which can be obtained. This latter point is beneficial in recovering rarer sequences.

The invention will now be further described and illustrated by means of the following Examples.

EXAMPLE 1

All oligonucleotides used in this Example were synthesised Trityl on, using an ABI 380B DNA Synthesizer, according to the manufacturers instructions. Purification was by reverse phase HPLC (see, for example, Becker, C., R., et al., J. Chromatography 326, p293–299 (1985)). Human brain and adrenal tissues were obtained from a mixture of 12 to 15 week menstrual age foetuses and then snap frozen in liquid nitrogen before storing in bijou bottles in a −80° C. freezer. The two types of tissue were used separately, directly from the freezer, to prepare cDNA from which restriction fragments were generated for sorting into subsets. 1 g of each of the separate tissues were homogenised, using an Ultra-Turrax T25 Disperser Janke and Kunkel, IKA-Labortechnik, on ice in the presence of 4M guanidinium isothiocyanate to solubilize macromolecules. RNA was isolated from each homogenate by using centrifugation to sediment it through ceasium trifluoroacetate. This was performed using the Pharmacia kit according to the manufacturers instructions, except that centrifugation was performed for 36 hours and the RNA obtained was finally desalted and concentrated by performing two ethanol precipitations in succession with two 70% ethanol washes after each precipitation. In each case, polyA$^+$ (mRNA) was isolated from 200 to 400 µg of the total RNA by binding it to magnetic oligodT coated beads (Dynal). Solution containing unbound material was removed from the beads, which were washed, and then mRNA eluted directly for use. mRNA isolation was performed in accordance with the manufacturers instructions. Yields of RNA from the beads were between 1 and 3% of the total RNA. 2 to 4 µg of the eluted RNA were used for cDNA synthesis. cDNA synthesis was performed according to the method of Gubler, U and Hoffman, B. J. Gene 25 p263 (1983) using a Pharmacia kit according to the manufacturers instructions. OligodT was used to prime the first strand cDNA synthesis reaction. The cDNA was purified by extracting twice with phenol/chloroform and then low molecular weight solutes including nucleic acids below ca. 300 bases were removed by passing the cDNA reaction mixture through a Pharmacia S400 spun column used according to the manufacturers instructions. Running buffer for the column comprised 10 mM Tris-HCl, 1 mM EDTA, 50 mM NaCl @pH 7.5.

The column eluate was adjusted to 10 mM Mg$^{2+}$ and then the purified cDNA was restricted by the action of 1 unit per 10 µl of the endonuclease Fok I at 37° C. for 1 hour, so that it would be able to accept adaptors.

The cDNA fragments were purified by two successive phenol/chloroform extractions followed by passing them through S400 spun columns as described above.

The adaptors used were oligonucleotides 5' N$_4$N$_4$N$_4$N$_4$TCCTTCTCCTGCGACAGACA with the complementary strand 5' TGTCTGTCGCAGGAGAAGGA and 5' AAN$_4$N$_4$TCTCGGACAGTGCTCCGAGAAC or 5' TTN$_4$N$_4$TCTCGGACAGTGCTCCGAGAAC each with the complementary 5' biotinylated strand GTTCTCGGAG-CACTGTCCGAGA. These were added to 25% of the eluted material by incubating together 200 pmoles of the mixture of double-stranded adaptors in the elution buffer to which had been added MgCl$_2$ to 10 mM, ATP to 10 mM and 0.025 units/µl of T4 DNA ligase. The oligonucleotide 5' biotinylated GTTCTCGGAGCACTGTCCGAGA, and whichever of the complementary oligonucleotides with which it was used, each comprised 1/32 of the molar proportion total adaptors. The final reaction volume was 90 µl which was heated to 65° C. for 3 minutes and then cooled to room temperature before the ligase was added. Ligation was performed for 16 hours at 12° C.

Two successive phenol/chloroform extractions were performed to remove the ligase. The final aqueous phase was passed through an S400 spun column (Pharmacia) as described above except that the column was used with 10 mM Tris pH 8.3/50 mM NaCl.

The column eluate was adjusted to 25 mMMg2+, 0.5 mM dNTPs in a final volume of 200 µl. The mixture was placed in a thermocycler (Techne MW2) and heated to 78° C. for 5 minutes. At this point 10 units of cloned Taq DNA polymerase (AmpliTaq, Perkin Elmer) were added. This was followed by an incubation at 72° C. for 10 minutes to fill in the unligated strand of the adaptor. After the second incubation 200 µl of streptavidin coated magnetic beads (Dynal) prepared according to the manufacturers instructions were added to bind cDNA ligated to that of the oligonucleotides which was complementary to the 5' GTTCTCGGAGCACT-GTCCGAGA biotinylated adaptor. Bead binding was allowed to proceed at 28° C. for 30 minutes with mixing every 10 minutes.

Un-biotinylated cDNAs were washed from the beads with 400 µl each of 2M NaCl twice, fresh 0.15 mM NaOH four times at 28° C. for 5 minutes each, water twice and finally a buffer comprising 20 mM Tris pH 8.3, 50 mM NaCl, and 25 mM Mg$^{2+}$. The beads were then resuspended in 240 µl of the final buffer including additionally 0.5 mM dNTPs and divided into 4×60 µl.

Four of the 60 µl aliquots, two from each tissue, were processed further specifically to prime and copy a subset of the immobilised, adaptoted fragments. 2 pmoles of the primer 5' CTGTCTGTCGCAGGAGAAGGAA were added to each of two aliquots, one from each tissue. 2 pmoles of the primer 5' CTGTCTGTCGCAGGAGAAGGAG were added to each of the other two aliquots. 2.5 units of Taq DNA polymerase were added to each reaction and 16 cycles of alternate denaturation at 95° C. for 30 seconds, annealing at 63° C. for 2 minutes and polymerisation at 72° C. for 3 minutes was performed to accumulate the selected single-strands in solution.

On completion of the DNA synthesis reactions a further 30 µl of resuspended beads were added to each reaction to remove the biotinylated fragments. The reaction was incubated at 28° C. for 30 minutes mixing every 10 minutes to ensure that the biotinylated strands were bead bound. Each aqueous phase containing the newly synthesised strands was then removed and extracted with phenol/chloroform twice to remove the enzyme before being further purified by passing through an S400 spun column equilibrated with 10 mM Tris pH 8.3/50 mM NaCl as described above.

Rounds of PCR amplification of subsets of the selected fragments were performed by using the original primer in each case, together with one of the primers 5' GTTCTCG-GAGCACTGTCCGAGAG or 5' GTTCTCGGAGCACT-GTCCGAGAC. This simultaneously rendered the fragments double-stranded and increased the amounts of available material. It was not known how many cycles of amplification would be required at this stage, since each primer pair would be expected to behave differently. It was therefore necessary directly to determine a suitable number empirically by using standard agarose gel electrophoresis to examine the reaction products after a given number of cycles. In some cases, to avoid the accumulation of non-specific products, it was necessary to perform an initial 5 cycles of amplification with both of the primers present at 2 pmoles each. All reactions were performed using 8 µl or 12.5% whichever was the larger but not exceeding 12 µl of the column effluent above. Reaction conditions were adjusted to 20 mM Tris pH 8.3, 50 mM NaCl, 25 mM Mg2+, 0.5 mM dNTPs and 2.5 units of Taq DNA polymerase in a final volume of 40 µl. Apart from when an initial amplification with 2 pmoles of each primer was performed, 20 pmoles of each primer were used. Cycles of amplification were performed at 95° C. for 30 seconds, 65° C. for 1 minute and 72° C. for 3 minutes.

For the purposes of cloning, selected cDNA was amplified as described immediately above, except that the reaction was not monitored. Instead, the number of cycles which had previously been shown to just give rise to all observable products plus another 4 cycles were performed. In addition, an extra 72° C. for 10 minutes incubation was performed after the last cycle.

The products of the reaction were then prepared for directional cloning. Water was added to adjust the final reaction volume to 60 µl. Enzyme was removed by two successive phenol/chloroform extractions. The final aqueous mixture was passed through an S400 column as described above, except that it had been equilibrated with 10 mM Tris HCl pH 7.5, 50 mM NaCl.

For directional cloning, advantage was taken of the different known sequences introduced at each end of the selected cDNAs by the adaptors in a modification of the method of Asiandis, C. and de Jong, P. J. (Nucl. Acids Res. 18, p6156 (1990)). Different cohesive ends were produced on each end by using the exonuclease activity of T4 DNA polymerase to resect from the 3' end, to the first T in each case. To 75 µl or 75% of the column eluate, whichever was least, were added 9.5 µl of 100 mM TrisHCl pH7.4, 100 mM MgCl2, and 9.5 µl of 0.5 mM dTTP. 16 units of T4 DNA polymerase were added and the reaction incubated in a water bath at 37° C. for 30 minutes. The enzyme was removed by extracting with phenol/chloroform, twice successively. The salt of the final aqueous phase was adjusted by passing it through an S300 column (Pharmacia) equilibrated with 10 mM TrisHCl pH 7.4, 1 mM EDTA as described above.

The *E. coli* plasmid cloning vector pBluescript KS+ (Alting-Meese, M. A. and Short J. M., Nucl. Acids Res. 17 p9494) was prepared for accepting the resected cDNA by restriction cleavage at the BamHI and HindIII sites and then adaptoting the resultant cohesive ends using the specific adaptors produced by the oligonucleotide 5' AGCTCG-GCTCGAGTCTG with its partially complementary oligonucleotide 5' GCGACAGACAGCAGACTCGAGCCG and the oligonucleotide 5' GATCCGGCTCGAGT with its partially complementary oligonucleotide 5' CCGAGAA-CACTCGAGCCG. Preparation of the vector and adaptoting were performed according to standard procedures. Insertion of the cDNA was performed between the BamHI and HindIII restriction sites. Recombinant vectors were transformed into the host XL1-Blue (Bullock, W. O. et al Biotechniques 5 p376–378 (1987)) by the method of Hannahan, D. J. (Mol. Biol. 166 p577–580 (1983)). Suitable standard controls for the ligations and transformations were also included.

Post transformation procedures were as described in "Molecular Cloning", 2nd Edition (Sambrook J., Fritsch, E. F., and Maniatis, T. CSH Press (1989)). Colonies were produced by plating onto X-gal/IPTG L-agar plates containing 50 µg/ml ampicillin and 10 µg/ml tetracyclin. Clear colonies were picked, each into a separate well of a microtitre plate, containing 100 µl of L-broth and 50 µg/ml ampicillin. Growth was allowed to occur for 16 hours at 37° C. 100 µl of 50% or 30% glycerol was added to plates which were archived at –20° C. or –80° C., respectively.

Bacteria corresponding to those archived were used for preparing templates for sequencing by the dideoxy method (Sanger, F. Milklen, S. and Coulson, A. R. Proc. Natl. Acad. Sci. 74 p5463–5467 (1977)). Bacteria for this purpose were either grown on L-agar plates containing 50 µg/ml of ampicillin, prepared at the same time as they had been grown in liquid culture, or after plating out from the archive. Alternatively, fresh liquid cultures were inoculated from the archive. In all cases, cDNA inserts were amplified for sequencing by PCR (Saiki, R. K. et al Science 239 p487–491 (1988)). PCR was either performed using bacteria directly added to the reaction, by a toothpick, or PCR was performed using 1/50th of the plasmid isolated by preparative methods (Holmes, D. S. and Quigley, M. Anal. Biochem. 114 p193 (1981)) from the bacteria in the liquid cultures or from the plates.

20 pmoles of each of the PCR primers 5' biotinylated GTAAAACGACGGCCAGT and 5' CGAGGTCGACGG-TATCG were used in 40 µl reactions containing 2.5 mM Mg$^{2+}$, 50 mM KCl, Tris-HCl pH 8.3 and 0.25 units of Amplitaq (Cetus). Reactions were performed at 95° C., for 1 minute, followed by 35 cycles at 95° C. for 30 seconds, 60° C. for 30 seconds and 72° C. for 40 seconds. After the cycles, a final incubation at 72° C. for 5 minutes was performed.

After PCR, standard agarose gel electrophoresis was used to determine which reactions had been successful. The biotinylated strands of successful reactions were then recovered for single-stranded sequencing bybinding them to steptravidin coated beads (Dynal) and then washing, all according to the manufacturers instructions, except that the washing steps were either performed manually or performed automatically in the 96 well microtitre plate format using a Biomek robotic work-station attached to a side-arm loader (Beckman).

Dideoxy chain termination sequencing reactions were performed using the immobilised, biotinylated strands as templates and 2 pmoles of the oligonucleotide 5' CGAG-GTCGACGGTATCG as primer. Reactions were performed using fluorescently-labelled terminators (Du Pont) or a fluoroscein-labelled primer (Pharmacia) according to the manufacturers instructions. Reactions were analyzed using automated DNA sequencers. A Genesis 2000 was used for the "Du Pont" reactions and an A.L.F. for the "Pharmacia" reactions. Bases were assigned for the Genesis 2000 reads using the manufacturers Base Caller software. Files of called bases were then transferred to a SUN Network from an Apple Macintosh computer which had been used for base calling. Raw data from the A.L.F. reads was directly transferred to a SUN network where bases were called using the public domain "trace editor software" (TED). In both cases, files of called bases were entered into a Sybase™ database. Entering data entailed automatically removing vector and adaptor or linker sequences, but not editing ambiguous bases. After removal of the unwanted bases, files were automatically compared to other sequences in the cDNA database and the latest versions of the publically available databases, GENBANK and SWISSPROT. Searches were performed with the "basic local alignment search tool" (BLAST) (Karlin, S. and Altschul, S. F. Proc. Natl. Acad. Sci. 87 p2264–2268 (1990)).

It was expected that the amplification products of different subsets would appear qualitatively different because different cDNA fragments would be present in each. This was confirmed by agarose gel electrophoresis. Furthermore, amplification products were dependent on cDNA having been used. The amplification products were unlikely to be artefacts because their average size decreased on amplification. The spun columns used selected against material below 300 base pairs. This material would therefore have been expected to have been present in low amounts and therefore be the last to appear with amplification explaining the decrease in average size. The most usual amplification artefacts are multimers whose average size increases on amplification, and this was not observed.

Thirty five sequences, picked at random, were scored for the presence of a FokI site at the correct distance from the selected bases. 10 (28.5%) gave no data because of ambiguous bases. 15 (60% of the remainder) did not have such a site, while 10 (40% of the remainder) did have the expected FokI site. This is entirely as expected because Fok 1 can either be internal to a cleavage (in which case it appears in the selected fragment) or it can be external (in which case it is removed from a selected fragment). There is an equal likelihood of either possibility assuming perfectly random nucleic acid distribution. When different isolates of the same fragment in different clones were observed, these were always found to have the same sense with respect to the adaptors used and the vector. This is extremely unlikely by random assortment, and only likely as a result of the process of this invention. When observed sequences were found to correspond to already known sequences, the Fok I fragments selected were found to be as expected having regard to the bases used for selection, for example, the FokI fragment between bases 2642 and 3039 of DNA corresponding to the mRNA of the human amyloid A4 mRNA.

EXAMPLE 2

Subsets of nucleic acid were prepared from cDNA as described in Example 1. cDNA was prepared from foetal liver as described in Example 1, in addition to the foetal adrenal and foetal brain cDNA already described in that Example.

The restriction digestion, adaptoring and priming for the liver subset were performed as described in Example 1. In particular, the adaptor which was used for ligating to a specific set of fragments was 5'TTNNTCTCGGACAGT-GCTCCGAGAAC and the primers used for priming of specific subsets during PCR of the specifically adaptored subsets were 5'CTGTCTGTCGCAGGAGAAGGAC (for the adaptor which had no ligation specificity for the required subset) and 5'GTTCTCGGAGCACTGTCCGAGAC (for the adaptor which was used to specifically select a subset of fragments). As a control, subsets were identically prepared without the addition of cDNA. 20 µl samples were taken after the final PCR reactions which produce the subsets and subjected to analysis by agarose gel electrophoresis, the nucleic acid being detected by ethidium bromide. The results are:

Lane 1—marker

Lane 2—as 6, no cDNA added

Lane 3—as 7, no cDNA added

Lane 4—as 8, no cDNA added

Lane 5—size marker: 2176, 1766, 1230, 1033, 653, 517, 453, 394, 298, 234 base pairs respectively, uppermost to lowermost visible bands Lane 6—fetal brain cDNA subset, adaptor specific for tt, specific adaptor primer specific for g, non specific adaptor primer specific for c Lane 7—fetal adrenal cDNA subset, adaptor specific for aa, specific adaptor primer specific for g, non specific adaptor primer specific for g Lane 8—fetal liver cDNA subset, adaptor specific for tt, specific adaptor primer specific for g, non specific adaptor primer for g It can be seen from lanes 2 to 4 and 6 to 8 that unless cDNA was added no amplification was observed, illustrating that de novo amplification, for example by primer dimerisation, is not a problem. Furthermore, in addition to the other products, a strong specific band was observed in the foetal liver and a different strong specific band in the foetal adrenal samples. Several weaker bands were observed in the foetal brain sample. This provided an opportunity to test the specificity of the sorting procedure.

The unused material was cloned as described in Example 1, and then individual clones were sequenced as described in Example 1. The sequence files from each of the subsets were separately copied from the database. The sequences from a given subset were then compared to each other using icaass, a global similarity comparison algorithm from the software icatools (Parsons, J et al CABIOS 4 p367–271 (1988)). This determined how often the same restriction fragment from the sorted cDNA was observed. By comparison to the BLAST searches, it could be deduced that assuming no significant cloning bias, 21.4% of the liver subset was the Fok 1 restriction fragment at the end corresponding to the carboxyl terminus of serum albumin (bases <2080 on Genbank accession no=L00132), and that this was the major band observed in the agarose gel. The size of the band is consistent with this deduction. There are 6 possible Fok 1 restriction fragments from serum albumin (which is an abundant transcript) so substantial selection by the sorting procedure had occurred. Similarly, the abundant restriction fragment in the adrenal subset (6.4%) originated from the mitochondria within the region of the gene for NADH-ubiquinone oxidoreductase chain 4 (bases >11711 on Genbank accession no=J01415). No restriction fragments dominated the brain subset. These results are also consistent with the agarose gel analysis and again indicate that selection has occurred.

Cloning was performed with an orientation with respect to the selective and the non-selective adaptors. This provides an additional test of the sorting procedure because, if no selection was occurring, when a fragment was observed more than once its orientation would be expected to be random, with 50% of instances in one orientation and 50% in the opposite orientation. In fact, the results given in Table 2 below show that when a fragment occurs more than once, as determined by the icaass comparison, in none out of 40 cases did antisense matches occur. This is highly improbable unless selection has introduced an orientation which has been maintained during the directional cloning. Selection was achieved through adaptor ligation and through priming, thus each of these must have had a high degree of specificity during the selection. The specificity of the ligation is remarkable given that the oligonucleotides in the ligation reaction covered every possible combination of bases at each of the four possible base positions closest to the 5' end of the non-specific adaptor. As a comparison the sequencing and analysis was performed as described in Example 1, except that conventional, commercial cDNA libraries which had not been sorted or directionally cloned were used as the source of the cDNA clones, and appropriate sequencing primers were used. The results for these comparisons are also shown in Table 2. It can be seen that antisense matches are commonly observed at a frequency of 10.5% and 36.3% in the adult liver (Clontech Laboratories, Inc Cat No HL1001b) and adult brain cortex (Clontech Laboratories, Inc Cat No HL 10036) libraries, respectively.

fragments produced from cDNA were present in a wide variety of different abundances, reflecting the original composition of the mRNA population. Nevertheless, sorting was successfully achieved, thus illustrating the robustness of the method.

The known directionality of sorted fragments makes it possible, in principle, to use fragments directly for probing by PCR. This would require that the same fragment be isolated from two identical subsets, except that the core sequences of the adaptors used for each subset would be different. The fragment from one set would then be immobilised at the 5' end of one of its adapter sequences and then annealed to the target. No annealing between target and fragment could occur at sequences which corresponded to

TABLE 2

Comparison of frequency classes and the proportion of antisense matches between cDNA subsets and total cDNA libraries.

|  | Subset | Subset | Subset | Subset | Subset | Total cDNA Libraries | |
|---|---|---|---|---|---|---|---|
| Tissue | Brain | Brain | Adrenal | Adrenal | Adrenal | Adult Liver | Adult Brain (cortex) |
| Adaptor specificity | aa | aa | aa | aa | tt | | |
| Primer for specific adaptor | a | g | a | g | a | | |
| Primer for non specific adaptor | g | g | g | g | g | | |
| Frequency class | | | | | | | |
| 1 | 183 | 117 | 58 | 163 | 38 | 226 | 341 |
| 2 | 14 | 2 | 2 | 2 | | 15 | 19 |
| 3 | 3 | 2 | | 2 | 1 | 4 | 3 |
| 4 | | | | | | | 1 |
| 5 | | | | | | | |
| 6 | | | | | | 1 | |
| 7 | | | | | | | 1 |
| 8 | | | | | | | 1 |
| 9 | | | | | | | 1 |
| 10 | | | | | | | |
| 11 | | | | | | | |
| 12 | | | | 1 | | | |
| 13 | | | | | | | 1 |
| 14 | | | | | | | |
| 15 | | | | | | | |
| 16 | | | | | | | |
| % unique patterns | 90.91% | 95.28% | 96.77% | 90.27% | 95.12% | 89.42% | 84.62% |
| Antisense matches | 0 | 0 | 0 | 0 | 0 | 10.5% | 36.3% |

Using the present process, once restriction fragments from an original nucleic acid have been sorted into subsets they can be advantageously manipulated and analysed by the full repertoire of molecular genetic or molecular biological techniques. They are also useful for a wide variety of applications which take particular advantage of their sorted nature. Compared to the situation in the original population, some of the useful types of property conferred on the fragments by sorting are that their relative abundance is higher in the sorted population, that the sequences at the ends of all of the members of a sorted population are the same and therefore indexed, that the members of a sorted population form a unique and discrete set, that the subset produced from one type of nucleic acid will be comparable to the same subset produced from a related nucleic acid, and that by separately recognizing the two ends of the fragments in a subset they acquire known directionality.

The application of the method for sorting restriction fragments produced from cDNAs in the human genome sequencing project is amongst the most technically demanding examples of the application of the present process which can be envisaged. Single-stranded RNA first had to be converted into double-stranded cDNA. Furthermore, the adaptors. A DNA polymerase, with a 3' exonuclease as its sole nuclease activity, would then be used to resect the unannealed 3' ends until the first complementary annealed base was reached, at which point the reverse complement of the non-immobilized adaptor sequence would become copied into the target. After resecting, the nucleic acids would then be heat denatured, simultaneously inactivating the enzyme, and the immobilized fragments removed to leave target which had incorporated the non-immobilized adaptor sequence. Copies of the target could then be made from a primer which corresponded to the incorporated adaptor. Target would then be denatured and annealed to the complementary strand of the fragment from the second subset. This fragment would also have been immobilized at its 5' end. Resecting would be performed as before. This time, the reverse complement of adaptor sequences on the target would become incorporated onto the immobilized fragment. Fragments which owed their origin specifically to the target could then be exclusively amplified by PCR using a primer which corresponded to the current immobilized 5' end and a primer which corresponded to the previous immobilized 5' end. It may be possible to use more than one type of fragment at once in this approach. Furthermore, exact complementarity between probe and target may not be required, thus allowing polymorphisms to be detected.

The fact that members of sorted populations form unique and discrete sets could be used more conveniently to identify fragments of interest. Fragments would be sorted into subsets such that any member of a subset could be detected using a suitable hybridization probe. Probing the subsets would identify in which subset a fragment of interest could be found. The fragments in that subset would then be probed to find the one of interest. This two step approach would be easier than probing all possible fragments at once.

The principle that members of sorted populations form unique and discrete sets can also be exploited during sequencing projects. Two or more different restriction endonucleases could be used to produce two or more corresponding sets of subsets in the knowledge that overlapping fragments must be produced between the sets of subsets. The members of each subset would then be sequenced. The degree of sorting would have been determined in advance to produce a number of fragments per subset that would allow each of the members to be easily identified. This would minimize the need repeatedly to read the same sequences, as commonly occurs during other approaches to sequencing projects. In addition, fewer gaps would be expected in the final overlapping sequence. It is often desirable to read a given sequence several times so that bases corresponding to ambiguities can be confirmed. This could easily be achieved by reading different isolates of the same fragment. Gaps would occur in the sequence either because inserts were too long to be sequenced or because fragments were of an inappropriate size to be successfully sorted. It would be possible conveniently to fill such gaps by using the known flanking sequence to predict in which subset a fragment produced by a different restriction endonuclease could be found for the purpose of extending the sequence. Fragments from the vector would also be present, but they could easily be avoided since it could be predicted in which subset they would occur and they could be identified from their size.

The fact that fragments are in a higher relative abundance in a sorted subset than in the original population is likely to benefit applications which use nucleic acid hybridization probes. In such applications, sensitivity is determined by "signal to noise" ratios. This becomes critical in applications where not all of the probe is specific for a particular target and can therefore contribute to background (thus reducing sensitivity).

A limit is therefore set on the size of a nucleic acid or the number of different nucleic acids which can be used simultaneously as a probe, which in turn reduces the possible range of applications. These limits can be overcome by using, separately. as probes, sorted subsets of the original intended probe. In this way, probing applications are made possible that otherwise would require detailed subcloning and/or characterisation of the original nucleic acid. Examples of nucleic acid types known in the art which could be used as probes or targets in any possible combination in this way include: cDNA fragments, clones or libraries; lambda genomic clones or libraries; cosmid genomic clones or libraries; P1 genomic clones or libraries; YAC genomic clones or libraries; sorted chromosomes or products of sorted chromosomes; chromosome specific libraries; products or libraries of material from microdisected chromosomes; products of co-incidence cloning or libraries of co-incidence clones; products of IRS-PCR or libraries of these products.

In general, the aim would be to detect sequences in common between the possible pairings. It would be particularly helpful when there were sequences of widely different abundance in the probe and/or target, since it would allow simultaneous detection of sequences that would not normally be possible as a result of wide differences in their signal strength. A classic example of such a situation is when differential screening of cDNA libraries is being performed. Typically, clones in two different cDNA libraries are detected using a probe prepared from the cDNAs used to make one of the libraries. The strength of the signal from a given clone indicates its abundance in the library to which the probe corresponds. Many clones will be an abundance which is too low to be detected. Appropriate enrichment of the probe in subsets through sorting would allow all clones to produce a measurable signal.

Given that, by sorting, the enrichment of fragments from a probe can be tailored so that even the least abundant sequence in a target can be detected, that the members of a sorted population form a unique and discrete set, and that the subset produced from one type of nucleic acid will be comparable to the same subset produced from a related nucleic acid, it is possible to fingerprint individual members of libraries of interest for the purpose of clone identification or mapping. This also requires that subsets are discretely, partially overlapping, which, as a result of both ends of any given fragment being independently sorted, they are. Each subset from a probe would be used in turn to detect clones in one or more libraries of interest. Each clone would then acquire a signature determined by the subsets which detected it. Resolution would depend on how many features were in a subset, how many subsets were produced and by the number of clones for which a signature was determined. A sufficient number of subsets could be produced by preparing them from more than one enzyme so that each clone could be given a unique signature through which it could be identified. Clones with the same signature could be assumed to have the same insert, while for the purposes of physical mapping, overlapping signatures would signify overlapping inserts.

A common requirement during genetic mapping projects, for example in clinical genetics, is to screen for bases which are polymorphic between individuals, so that the fate of the genomic region in which the polymorphism are found can be monitored through generations for linkage analysis. Restriction site polymorphisms are useful in this respect. Base polymorphisms can result in individuals differing with regard to whether they possess a detectable restriction site. The twin principles that the members of a sorted population form a unique and discrete set and that the subset produced from one type of nucleic acid will be comparable to the same subset produced from a related nucleic acid provide a convenient means of detecting clones which themselves can be used as probes to detect polymorphisms at restriction sites between individuals. Clones would be prepared from the fragments in a subset from one individual. These would then be probed using the fragments which were used to produce the clones, and also separately probed using fragments from the corresponding subset prepared from a different individual. Clones which could detect restriction site polymorphisms between the individuals would be identified as those which failed to give rise to a signal when the subset from the individual from which they did not originate was used as a probe as compared to when the subset from the individual from which they did originate was used as a probe. The polymorphism would be in a site for the enzyme which was originally used to prepare the subset. Clones of genomic or cDNA could be used for the application. Use of cDNA clones would have the advantage that it would be known that the restriction site polymorphisms were being detected in actual genes, whose fate could then be followed through generations.

It would be particularly advantageous if the individuals between whom the polymorphisms were detected as described above were those who corresponded to the grandparents in a back-cross. 50% of the individuals in the F2 generation could then be scored for the polymorphisms detected, assuming that back-crossing had been performed equally to each of the original grandparents. It would also be useful if the nucleic acid from each of the F2 individuals was separately sorted and amplified. Polymorphisms could then be scored in the amplified F2 subsets corresponding to these in which the polymorphisms were detected between the original grandparents. This would have the triple advantage that the usually finite back-cross resource would have been immortalized for this purpose, that the present or absent nature of signal from each sample would allow many samples to be conveniently probed simultaneously after spotting them onto a gridded array, and that the target, where present, would have been enriched in a subset so that it could be more easily detected. This could be of particular value in plant or animal breeding.

In view of the above, it will be understood that the invention includes any use of a method of the invention or of a population of sequences, sorted or categorised in accordance with the invention, where said use takes advantage of any one or more of:

(a) the relatively higher abundance of sequences in a sorted population;

(b) the "indexing" of sorted sequences by the use of adaptors;

(c) the fact that members of a sorted population form a unique and discrete set;

(d) the fact that a given subset produced from one nucleic acid source material will be comparable to the correspondingly "adaptored" subset from a related nucleic acid; and, (e) as a result of adaptoring sequences acquire a known directionality.

Without prejudice to the generality of the foregoing, the invention includes, inter alia, the use of adaptored and sorted sequences as PCR probes; the use of the present method to facilitate investigation of a population of sequences to identify a preselected fragment or sequence of interest; the use of the present method to sort or categorise (eg for sequencing purposes) sets of sequences produced by exposing a nucleic acid source material to the action of restriction endonucleases; the use of the present method to increase the abundance of any given sequence in a population thereby to facilitate investigation by a hybridization probe; the use as a hybridization probe of a sorted subset (or subsets) of sequences; the use of the present method in clone identification or mapping; and, the use of the present method in examining in a species sequence polymorphisms, optionally monitored through more than one generation of the species in question.

It will be appreciated that the above is not exhaustive, and it should not be construed as limiting on the applicability of the present pioneering invention.

In other aspects, the invention obviously includes:

(a) The use of a population of adaptor molecules, each of such molecules carrying a nucleic acid sequence end recognition means, in categorizing or sorting a nucleic acid sample into predetermined subsets of nucleic acid sequences, wherein each such adaptor molecule carries a nucleic acid sequence end recognition means which is specific to a predetermined base.

(b) A kit including reagents for use in a nucleic acid categorization process and comprising a population of adaptor molecules in the form of double stranded oligonucleotides having a single stranded end extension as a nucleic acid sequence end recognition means.

(c) A kit as above, wherein:
(i) the adaptor molecule nucleic acid sequence end recognition means recognizes a predetermined base, the presence of which base can form the basis for selection and/or
(ii) the primers (if present) include within their sequence a predetermined base, the presence of which base can form the basis for selection.

(d) A population of adaptor molecules for use in a nucleic acid categorization process, wherein the adaptor molecules include nucleic acid sequence end recognition means recognising a predetermined base thereby permitting categorization of nucleic acid sequences linked to said adaptor molecules on the basis of selecting for a subset in which a chosen one of said predetermined bases has been recognized.

(e) A process for the categorization of nucleic acid sequences in which said sequences are linked to a population of adaptor molecules each exhibiting specificity for linking to a sequence including a predetermined nucleotide base, categorization of the resulting linked sequences being based upon selection for the base.

I claim:

1. A process for categorizing uncharacterized nucleic acid by sorting said nucleic acid into sequence-specific subsets comprising:

(a) optionally, cleaving said uncharacterized nucleic acid by the action of a reagent, which reagent cleaves said nucleic acid to produce smaller size cleavage products;

(b) reacting either the uncharacterized nucleic acid or said cleavage products from (a) with a first population of adaptor molecules to generate first adaptored products, each of which first adaptor molecules comprises a nucleic acid sequence end recognition means, wherein said population of first adaptor molecules comprises a range of such molecules having sequence end recognition means linking, when present, to a first predetermined subset of said uncharacterized nucleic acid sequences to form first adaptored products;

(c) selecting and separating said first adaptored products resulting from (b);

(d) cleaving adaptors from the selected and separated first adaptored products from (c) to form first selected nucleic acids;

(e) reacting said first selected nucleic acids resulting from (d) with a second population of adaptor molecules to generate second adaptored products, each of which second adaptor molecules comprises nucleic acid end recognition means, wherein said second population of adaptor molecules comprises sequence end recognition means linking to a second predetermined subset of nucleic acid sequences to form second adaptored products; and (f) selecting and separating said second adaptored products resulting from (e).

2. A process of claim 1, wherein the cleavage reagent is an endonuclease.

3. A process of claim 1, wherein the first or second adaptor molecules include oligonucleotides in which the nucleic acid sequence end recognition means comprises a single stranded end of known nucleotide composition.

4. A process of claim 3, wherein the single stranded end exhibits complementarity to a single predetermined nucleotide.

5. A process of claim 1, wherein the first or second population of adaptor molecules includes individual molecules such that both ends of the uncharacterized nucleic acid or cleavage products can be linked thereto.

6. A process of claim 1, wherein at least some of the first and/or second adaptor molecules are adapted to be immobilized on a solid phase.

7. A process of claim 1, wherein selection of first and/or second adaptor products is based upon selecting those adaptor molecules having a single predetermined base.

8. A process of claim 1, wherein optional step (a) is effected using an endonuelease specific to double stranded nucleic acid.

9. A process of claim 8, wherein the endonuclease is selected from the group consisting of BstNI, Ddel, Hgal, Hinfl and MnlI.

10. A process of claim 1, wherein at least some of the first or second adaptor molecules also comprise a known sequence permitting hybridization with a PCR primer.

11. A process of claim 9, wherein selection of first or second adaptored products is based upon selecting products subjected to priming of nucleic acid synthesis in which a primer has a single predetermined base.

12. A process of categorizing uncharacterized nucleic acid, comprising:

(a) cleaving said uncharacterized nucleic acid using an endonuclease which has cleavage and recognition site separated to cleave said nucleic acid to produce double stranded cleavage products, the individual strands of which overlap at cleaved ends to leave a single strand extending to a known extent;

b) ligating the cleavage products from (a) with first adaptor molecules to generate first adaptoted cleavage products, each of which first adaptor molecules has a cleavage product end recognition sequence wherein the thus-used first adaptor molecules comprise a range of adaptor molecules having recognition sequences complementary to a first predetermined subset of the sequences of the cleavage generated extending single strands resulting from (a);

(c) selecting and separating the first adaptored cleavage products from (b) which carry an adaptor of first known recognition sequence;

(d) cleaving first adaptor molecules from the selected and separated products from (c) to form first selected nucleic acids;

(e) ligating the first selected nucleic acids from (d) with second adaptor molecules to generate second adaptoted cleavage products, each of which second adaptor molecules has a cleavage product end recognition sequence wherein the thus-used second adaptor molecules comprise a range of adaptor molecules having recognition sequences complementary to a second predetermined subset of the sequences of the cleavage-generated extending single strands resulting from (d); and (f) selecting and separating the second adaptoted cleavage products from (e) which comprise an adaptor of second known recognition sequence.

13. A process of claim 12, wherein in step (b) or step (e) a number of separate reactions are performed in each of which a subset of the range of adaptor molecules is ligated.

14. A process of claim 12, wherein the uncharacterized nucleic acid is a single stranded nucleic acid which is first converted to double stranded nucleic acid.

15. A process of claim 12, wherein an endonuclease is employed in step (a) which is chosen from Class II restriction endonueleases acting on cleavage sites which are asymmetrically spaced across the two strands of a double stranded substrate, and the specificity of which is not affected by the nature of the bases adjacent to a cleavage site.

16. A process of claim 15 wherein the endonuelease is Fok 1.

17. A process of claim 15, wherein the cleavage products from (a) have extending single strands which are from 1 to 10 bases in length.

18. A process of claim 17, wherein said extending single strands resulting from (a) are from 4 to 6 bases in length.

19. A process of claim 12, wherein the first and/or second adaptor molecules have cleavage product end recognition sequences which comprise extending single strands which are complementary to the cleavage product extending single strands resulting from step (a) and/or step (e).

20. A process of claim 19, wherein at least some first and/or second adaptor molecule cleavage product end recognition sequences end with a 5' hydroxyl group.

21. A process of claim 12, wherein first or second adaptor molecule cleavage product end recognition sequences are at least three nucleotides in length with unselected random bases present at each position two or more nucleotides in from the end.

22. A process of claim 12, wherein the first or second adaptor molecules also comprise a portion permitting separation when a nucleic acid sequence is attached to its adaptor.

23. A process of claim 22, wherein the portion permitting separation includes a biotin residue.

24. A process of claim 12, wherein selection of first and/or second adaptored products is based upon selecting those first or second adaptor molecules having a single predetermined base.

25. A process of claim 12, wherein the first or second adaptor molecules also comprise a predetermined core sequence so that nucleic acid sequences which have been linked to such molecules can be amplified by the use of a primer exhibiting complementarily to the core sequence.

26. A process of claim 25, wherein selection of adaptored products in (c) and/or (f) is based upon selecting products subjected to priming of nucleic acid synthesis in which a primer has a single predetermined base.

27. A process of claim 12, wherein adaptor molecules are employed in (b) which include a range of adaptor molecules having recognition sequences complementary to all possible members of a chosen subset of cleavage products present after step (a).

28. A process of claim 12, wherein adaptor molecules are employed in (e) which include a range of adaptor molecules having recognition sequences complementary to all possible members of a chosen subset of cleavage products present after step (d).

29. A process of claim 12, wherein at least some of the first and/or second adaptor molecules carry a predetermined recognition sequence which differs from that of all other adaptors present.

30. A categorizing nucleotide sequence population kit, comprising a population of adaptor molecules in the form of double stranded oligonucleotides having a single stranded end extension as a nucleic acid sequence end recognition means and primers for use in a nucleic acid amplification process, optionally wherein at least some of the adaptor molecules includes a sequence for primer hybridization thereto, wherein the single stranded end extension of said adaptor molecules have recognition means complementary to all possible members of a chosen subset of nucleic acids to be categorized.

31. A kit as claimed in claim 30, wherein:
   (a) the adaptor molecule nucleic acid sequence end recognition means recognizes a predetermined base, the presence of which base can form the basis for selection, and/or
   (b) the primers include within their sequence a predetermined base, presence of which base can form the basis for selection.

32. A kit of claim 30, wherein the adaptor molecules include nucleotide sequence which, in use, not only permits indexing of nucleic acid sequences linked to said adaptor molecules but also establishes directionality in said nucleic acid sequences.

33. A kit of claim 30, wherein at least some of the adaptor molecules also include means permitting immobilization on a solid phase of such adaptor molecules when linked to nucleic acid sequences.

34. A kit of 30, and also including a nucleic acid cleavage reagent.

35. A process for the categorization of nucleic acid sequences in which said sequences are linked to a population of adaptor molecules each exhibiting specificity for linking to a sequence including a single predetermined nucleotide base, categorization of the resulting linked sequences being based upon selection for the single predetermined nucleotide base.

36. A process of categorizing uncharacterized nucleic acid comprising:
   (a) cleaving said uncharacterized nucleic acid of an endonuclease having cleavage and recognition site separated, to produce double stranded cleavage products having individual strands of which overlap at cleaved ends to leave a single strand extending to a known length;
   (b) ligating the cleavage products from (a) with adaptor molecules to generate adaptored cleavage products, each of which adaptor molecules has a cleavage product end recognition sequence, wherein the thus-used adaptor molecules comprise a range of adaptor molecules having recognition sequences complementary to a predetermined subset of the sequences of the cleavage-generated extending single strands; and
   (c) selecting and separating adaptored cleavage products resulting from (b) which comprise an adaptor of known recognition sequence wherein said selecting is based upon a chosen base or bases in said recognition sequence which is/are other than the entirety of said recognition sequence.

37. A process for categorizing uncharacterized nucleic acid by sorting said nucleic acid into sequence-specific subsets comprising:
   (a) optionally, initially cleaving said uncharacterized nucleic acid with a reagent, which cleaves said nucleic acid to produce smaller size cleavage products;
   (b) reacting either the uncharacterized nucleic acid or cleavage products from (a) with a population of adaptor molecules to generate adaptored products, each of which adaptor molecules comprises a nucleic acid sequence end recognition means, wherein said population of adaptor molecules comprise a range of such molecules having sequence end recognition means linking, when present, to a predetermined subset of nucleic acid sequences; and
   (c) selecting and separating adaptored products resulting from (b) which include an adaptor of chosen nucleic acid sequence end recognition means, wherein said selecting is based upon a chosen base or bases in the nucleic acid sequence which is recognized by said nucleic acid end recognition means, which base or bases is/are other than the entirety of said recognized nucleic acid sequence.

38. A method of categorizing or sorting a mixture of uncharacterized nucleic acids into a predetermined subset of nucleic acid sequences, comprising:
   linking, when present, a predetermined subset of nucleic acid sequences of said uncharacterized nucleic acids to a population of adaptor molecules, wherein each adaptor molecule contains a nucleic acid sequence end recognition means recognizing a single and same predetermined base, to form an adaptored product, thereby permitting categorization of said mixture of uncharacterized nucleic acid sequences on the basis of selecting for a subset in which said same and single predetermined base has been recognized, and
   selecting and separating said adaptored product.

39. A process of claim 38, wherein the adaptor molecules are double stranded oligonucleotides having a single stranded extension portion at an end which serves as the nucleic acid sequence end recognition means.

40. A process of claim 38, wherein the adaptor molecules also include a sequence permitting hybridization with a primer for nucleic acid amplification of any nucleic acid sequence linked to the adaptor molecules.

41. A kit of claim 30 further comprising of adaptor molecules, wherein the adaptor molecules comprise a nucleic acid sequence end recognition means recognizing a single predetermined base, thereby permitting categorization of nucleic acid sequences linked to said adaptor molecules on the basis of selecting for a subset in which said single predetermined base has been recognized.

* * * * *